US012409193B2

(12) United States Patent
Parker (10) Patent No.: US 12,409,193 B2
(45) Date of Patent: Sep. 9, 2025

(54) SYSTEMS, DEVICES, AND METHODS FOR SEPARATING AND WASHING MICROORGANISMS

(71) Applicant: DUKE UNIVERSITY, Durham, NC (US)

(72) Inventor: William Parker, Durham, NC (US)

(73) Assignee: DUKE UNIVERSITY, Durham, NC (US)

(*) Notice: Subject to any disclaimer, the term of this patent is extended or adjusted under 35 U.S.C. 154(b) by 960 days.

(21) Appl. No.: 17/296,908

(22) PCT Filed: Nov. 27, 2019

(86) PCT No.: PCT/US2019/063624
§ 371 (c)(1),
(2) Date: May 25, 2021

(87) PCT Pub. No.: WO2020/113013
PCT Pub. Date: Jun. 4, 2020

(65) Prior Publication Data
US 2022/0023352 A1 Jan. 27, 2022

Related U.S. Application Data

(60) Provisional application No. 62/771,733, filed on Nov. 27, 2018.

(51) Int. Cl.
*A61K 35/62* (2006.01)
*A01K 67/30* (2025.01)
*C12M 1/00* (2006.01)

(52) U.S. Cl.
CPC .............. *A61K 35/62* (2013.01); *A01K 67/30* (2025.01); *C12M 47/04* (2013.01)

(58) Field of Classification Search
CPC ...... A61K 35/62; A01K 67/033; C12M 47/04
USPC ....................................... 435/283.1
See application file for complete search history.

(56) References Cited

U.S. PATENT DOCUMENTS

| | | | |
|---|---|---|---|
| 5,804,072 A * | 9/1998 | Yang | B01D 29/606 210/111 |
| 6,416,716 B1 | 7/2002 | Shukla et al. | |
| 7,189,370 B2 * | 3/2007 | Liu | B01L 3/502746 422/50 |
| 10,107,729 B2 | 10/2018 | Gjerde | |
| 2008/0071071 A1 * | 3/2008 | LaBaer | G01N 33/6803 536/23.1 |
| 2016/0223441 A1 * | 8/2016 | Gjerde | C12N 5/061 |
| 2017/0002308 A1 * | 1/2017 | Liu | C12M 41/40 |

OTHER PUBLICATIONS

Smyth, K. et al. (2017). "Production and Use of Hymenolepis diminuta Cysticercoids as Anti-Inflammatory Therapeutics." J Clin Med. 6(98). 1-20. (Year: 2017).*

(Continued)

*Primary Examiner* — Jill A Warden
*Assistant Examiner* — Jacqueline Brazin
(74) *Attorney, Agent, or Firm* — Casimir Jones, S.C.; Rikki A. Hullinger (57) ABSTRACT

The present disclosure provides materials and methods for separating organisms from various other components of a composition. In particular, the present disclosure provides devices, systems, and methods for separating and washing helminths from contaminants such as bacteria.

19 Claims, 4 Drawing Sheets

(56) References Cited

OTHER PUBLICATIONS

International Search Report and Written Opinion for PCT/US2019/063624. Mailed Jan. 24, 2020. 9 pages.

Smyth et al., Production and Use of Hymenolepis diminuta Cysticercoids as Anti-Inflammatory Therapeutics. J Clin Med. Oct. 24, 2017;6(10):98.

Bono-Lunn, D. et al., Policy and regulations in light of the human body as a 'superorganism' containing multiple, intertwined symbiotic relationships. Clinical Research and Regulatory Affairs. 2016;33(2-4):39-48.

Cheng AM, et al. Overcoming evolutionary mismatch by self-treatment with helminths: current practices and experience. Journal of Evolutionary Medicine. 2015;3:Article ID 235910. 1-22.

Fumagalli, M, et al. Parasites represent a major selective force for interleukin genes and shape the genetic predisposition to autoimmune conditions. J Exp Med. Jun. 8, 2009;206(6):1395-408.

Helmby H. Human helminth therapy to treat inflammatory disorders—where do we stand? BMC Immunol. Mar. 26, 2015:16:12.

Khan, AR, et al. Helminth therapies: translating the unknown unknowns to known knowns. Int J Parasitol. Mar. 2013;43(3-4):293-9.

Liu J, et al. Practices and outcomes of self-treatment with helminths based on physicians' observations. J Helminthol. May 2017;91(3):267-277.

Parker W, et al. Evolutionary Biology and Anthropology Suggest Biome Reconstitution as a Necessary Approach toward Dealing with Immune Disorders. Evol Med Public Health. Jan. 2013;2013(1):89-103.

Pi, C. et al. Increased biodiversity in the environment improves the humoral response of rats. PLoS One. Apr. 8, 2015;10(4):e0120255.

Wolff, MJ, et al. Helminthic therapy: improving mucosal barrier function. Trends Parasitol. May 2012;28(5):187-94.

Zaccone P, et al. Parasitic worms and inflammatory diseases. Parasite Immunol. Oct. 2006;28(10):515-23.

\* cited by examiner

Wash hold section (triple)

FIG. 4A

Wash hold section (single)

SYSTEMS, DEVICES, AND METHODS FOR SEPARATING AND WASHING MICROORGANISMS

RELATED APPLICATIONS

This application claims priority to U.S. Provisional Patent Application No. 62/771,733, filed Nov. 27, 2018, which is incorporated herein by reference in its entirety.

FIELD

The present disclosure provides materials and methods for separating organisms from various other components of a composition. In particular, the present disclosure provides devices, systems, and methods for separating and washing helminths from contaminants such as bacteria.

BACKGROUND

Biota depletion theory, once known as the "hygiene hypothesis," describes the loss of contact with ancient symbionts that regulate immune and leads to pathogenic inflammation. Increasing evidence indicates that reintroduction of certain ancient symbionts, particularly intestinal worms or helminths, can restore adequate immune regulation. Controlled studies in animal models and the examination of folk medicine practices with helminths suggest that helminth therapy may be effective at treating inflammation-associated neuropsychiatric disorders as well as other conditions such as multiple sclerosis and inflammatory bowel disease.

Helminthic therapy offers the possibility of decreasing inflammation via immunomodulation rather than immunosuppression, and likely also improves mucosal barrier function. The scientific rationale behind this therapy is based on the long co-evolutionary history of helminths with their vertebrate hosts. Forces driving that coevolution include advantages to both host and helminth in minimizing the impact of helminth colonization on host fitness. This evolutionary process has resulted in the existence of helminths which are benign under conditions of adequate nutrition but yet modulate host immune function in a manner that decreases inflammation without impairing immune function.

Although "helminthic therapy" is likely effective for treatment of conditions such as multiple sclerosis and a range of allergic disorders, logistical problems with obtaining helminths for medical use have severely limited the utility of the therapy. *Hymenolepis diminuta* cysticercoids (HDCs) offer several advantages over other helminths currently under consideration. They are non-communicable, generally benign, easily produced, derived from edible insects (grain beetles, the intermediate hosts), and, similar to probiotics, do not leave the lumen of the gut. Further, extensive socio-medical studies examining folk-medicine practices of "self-treatment" with helminths have provided starting points for consideration of dosage, frequency of exposure, and disease indication for the use of these organisms as therapeutic agents. Given the tremendous potential therapeutic benefit and minimal patient risk, there is a clear need to develop a materials and methods for separating helminths that are capable of meeting FDA guidelines to advance this therapy to clinical trial and ultimate patient benefit.

SUMMARY

Embodiments of the present disclosure include organism separation devices. Organism separation devices as described herein include a column having a first end for receiving a plurality of organisms and a second end distal to the first end. The organism separation device further includes a fluid inlet port proximal to the second end of the column for receiving washing fluid, and a waste outlet port proximal to the first end of the column. The washing fluid flows from the fluid inlet port to the waste outlet port, and the plurality of organisms passes from the first end to the second end of the column. The flow of the washing fluid through the device is counter to that of the plurality of organisms.

In some embodiments, the first end comprises a first opening for receiving the plurality of organisms and the second end comprises a second opening for collecting the plurality of organisms. The diameter of the first opening may be greater than the diameter of the second opening.

In some embodiments, the column further includes a slow flow section proximal to the first end of the column, a rapid flow section proximal to the second end of the column and having a diameter that is less than the slow flow section, and a tapered wash hold section positioned between the slow flow section and the rapid flow section. The tapered wash hold section may comprise a single tapered segment. Alternatively, the tapered wash hold section may comprise two or more tapered segments that taper towards the second end of the column.

In some embodiments, the organism separation device further includes a valve positioned between the fluid inlet port and the second end. In some embodiments, the organism separation device further includes a removable cap that covers the first end.

In some embodiments, the organism separation device further includes a pump in fluid connection with the fluid inlet port for actively transporting the washing fluid from the fluid inlet port towards the waste outlet port.

In some embodiments, the organism separation device further includes a removable collection vial positioned at the second end of the column.

In some embodiments, the organism separation device further includes a solid support for holding the column in a vertical position.

Embodiments of the present disclosure further include systems comprising a plurality of organism separation devices as described herein. In some embodiments, the devices are arranged in parallel.

In some embodiments, the system further includes a pump in fluid connection with the fluid inlet port for two or more of the devices in the system. In such embodiments, the pump actively transports the washing fluid from the fluid inlet ports to the waste outlet ports of the two or more devices.

Embodiments of the present disclosure further include methods for separating a plurality of organisms. The methods include applying a composition comprising a plurality of organisms to an organism separation device or system described herein. In some embodiments, the method includes applying the composition to the first end of the washing device while the washing fluid is actively transported from the fluid inlet port to the waste outlet port at a first flow rate, reducing the flow rate from the fluid inlet port to a second flow rate, and collecting the plurality of organisms from the second end of the column. In some embodiments, the plurality of organisms collected from the second end of the column have been separated from at least one other component in the washing fluid. For example, the plurality of helminths collected from the second end of the column may be substantially free of bacteria.

In some embodiments, the washing fluid comprises at least 0.5% protein (w/w). In some embodiments, the plurality of organisms are helminths. For example, the helminths may be *Hymenolepis diminuta* cysticercoids (HDCs).

Embodiments of the present disclosure further include a composition comprising separated helminths obtained using the devices, systems, and methods described herein.

DETAILED DESCRIPTION

The present disclosure provides materials and methods for separating organisms. In some embodiments, the present disclosure provides devices, systems, and methods for separating helminths from one or more contaminants, such as bacteria.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Correlated to" as used herein refers to compared to.

"Helminth" as used herein refers to parasitic worms. The term helminth includes any suitable class of worm, including flukes (trematodes), tapeworms (cestodes), and roundworms (nematodes). The helminth may be any suitable species. A helminth as used in accordance with the devices, systems, and methods described herein may be at any suitable life stage (e.g., egg stage, larval stage, or adult stage).

"Intermediate host" as used herein refers to the life form from which the plurality or organisms are obtained directly prior to use in the systems, devices, and methods described herein. For example, the intermediate host may be the life from which a plurality of helminths are obtained. Suitable intermediate hosts include insects. For example, the intermediate host may be an edible beetle, such as a grain beetle. In some embodiments, the intermediate host may be purposefully infected with helminths that were previously obtained from a "primary host". The selection of the primary host will depend on the intended species of helminths to be used. For example, the "primary host" may be a rodent which is infected with helminths and adult stage helminths are allowed to grow. The primary host may then become a source of helminth eggs, which may be provided to the intermediate host. The eggs may develop into the therapeutic life stage of the helminth within the intermediate host. For example, *Hymenolepis diminuta* (rat tapeworm) may be allowed to grow to adult stage and produce eggs within a rat (e.g., the primary host) and the eggs, which may be obtained from the primary host through fecal matter, may be provided to the intermediate host by allowing the intermediate host to ingest the fecal matter containing the eggs. Subsequently, the eggs may develop into *Hymenolepis diminuta* cysticercoids (e.g., the therapeutic, larval stage of *Hymenolepis diminuta*) in the intermediate host prior to isolating from the intermediate host and subsequent use in the systems, devices, and methods described herein.

"Separating" as used herein refers to isolating a plurality organisms from a composition comprising the plurality of organisms and one or more contaminants. In some embodiments, separating refers to isolating a plurality of organisms from a composition containing contaminants remaining after the initial extraction of the organisms from an intermediate host, such as an insect. For example, contaminants may include cellular debris from the intermediate host (e.g., exoskeletal matter, internal organ matter, etc.) bacteria, and the like. In some embodiments, separating refers to isolating a plurality or organisms from bacteria. Separating a plurality or organisms may remove 50% or more of the contaminants from the composition comprising the plurality or organisms. For example, separating may remove 50%, 55%, 60%, 65%, 70%, 75%, 80%, 85%, 90%, 95%, 99%, or substantially all contaminants from the composition comprising the plurality or organisms.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (e.g., a monkey, such as a cynomolgus or rhesus monkey, chimpanzee, etc.) and a human). In some embodiments, the subject may be a human or a non-human. In one embodiment, the subject is a human. The subject or patient may be undergoing various forms of treatment. In some embodiments, the subject may ingest separated helminths for various therapeutic purposes. For example, a subject may ingest separated helminths for the purpose of treating one or more diseases or conditions.

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a treatment to a subject that is not at the time of administration afflicted with the disease. "Preventing" also refers to preventing the recurrence of a disease or of one or more symptoms associated with such disease.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. Organism Separation Device and Systems

Embodiments of the present disclosure include organism separation devices and systems. The devices and systems described herein may be used for separation of a plurality organisms from one or more contaminants. For example, the devices and systems described herein may be used for separation of organisms from contaminants remaining after extracting the organisms from an intermediate host. For example, the organisms may be extracted from a suitable intermediate host, such as an insect. For example, organisms may be extracted from edible beetles (e.g., grain beetles). The organisms may be applied to the devices or systems described herein to separate the organisms from contaminants remaining after the initial extraction from the intermediate host, including cellular debris (e.g., exoskeletal matter, internal organ matter, etc.), bacteria, and the like.

Figure 2:
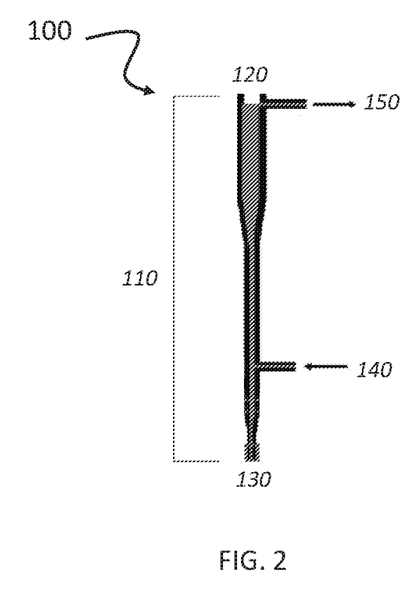
FIG. 2 is a representative drawing of one embodiment of an organism separation device (100), as described further herein.

FIG. 2 is a representative drawing of one embodiment of an organism separation device (100) described herein. The device (100) comprises a column (110) having a first end (120) for receiving a plurality of organisms and a second end (130) distal to the first end. The device (100) comprises a fluid inlet port (140) proximal to the second end of the column for receiving washing fluid, and a waste outlet port (150) proximal to the first end of the column. Washing fluid flows from the fluid inlet port (140) to the waste outlet port (150), and the plurality of organisms passes from the first end (120) to the second end (130) of the column (110).

Figure 3:
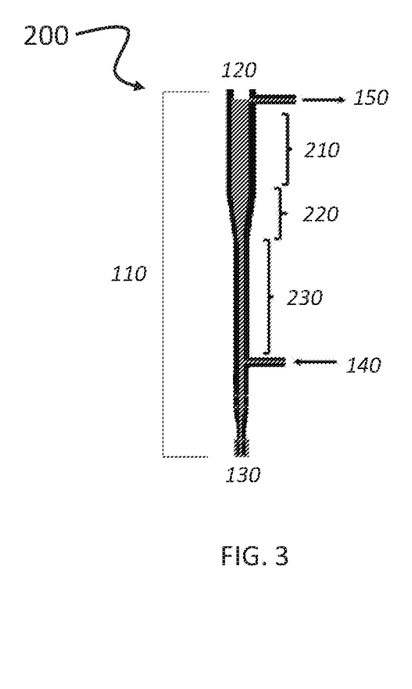
FIG. 3 is a representative drawing of another embodiment of an organism separation device (200), as described further herein.

FIG. 3 is a representative drawing of one embodiment of an organism separation device (200). The device comprises a column (110) having a first end (120) for receiving a plurality of organisms and a second end (130) distal to the first end. The device (200) comprises a fluid inlet port (140) proximal to the second end of the column for receiving washing fluid, and a waste outlet port (150) proximal to the first end of the column. Washing fluid flows from the fluid inlet port (140) to the waste outlet port (150), and the plurality of organisms passes from the first end (120) to the second end (130) of the column (110). The column (110) includes a slow flow section (210) proximal to the first end of the column, a rapid flow section (230) proximal to the second end of the column and having a diameter that is less than the slow flow section; and a tapered wash hold section (220) positioned between the slow flow section and the rapid flow section.

The column may comprise any suitable material to allow for flow of the plurality of organisms from the first end of the column towards the second end of the column while avoiding undesired sticking of the organisms to a surface of the column. For example, the column may comprise glass. As another example, the column may comprise plastic. In some embodiments, the column is coated with one or more materials to further prevent sticking of the organisms to a surface of the column. Desirable coatings would prevent sticking without presenting a danger of the coating degrading over time and contaminating the separated helminths (e.g., the helminths to be subsequently consumed by a subject) with potentially hazardous material for human consumption.

The separation device further comprises a fluid inlet port proximal to the second end of the column for receiving washing fluid. The washing fluid may be any suitable fluid for separating the plurality or organisms. Suitable washing fluids include, for example, protein-containing solutions. The washing fluid may contain 0.005% or more protein (w/w). For example, the washing fluid may contain at least 0.005%, 0.01%, 0.02%, 0.03%, 0.04%, 0.05%, 0.06%, 0.07%, 0.08%, 0.09%, 0.1%, 0.25%, 0.5%, 0.75%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% protein. In some embodiments, the washing fluid comprises a fluid suitable for consumption by a subject, such as a human. In some embodiments, the washing fluid may comprise milk. For example, the washing fluid may comprise almond milk, bovine milk, rice milk, soy milk, cashew milk, oat milk, or other forms of milk containing a suitable protein content. In some embodiments, the washing fluid may be clarified in order to allow for visual observation of the helminths within the column. For example, milk may be clarified by freeze-thawing the milk, followed by centrifugation and removal of the supernatant, leaving clarified liquid that still possesses a suitable protein content to prevent sticking of the helminths to the device.

The separation device further comprises a waste outlet port proximal to the first end of the column. The washing fluid flows from the fluid inlet port towards the waste outlet port. The washing fluid thus flows counter to the flow of the organisms, which travel from the first end towards the second end of the column. As the flow of the washing fluid is counter to the force of gravity, the washing fluid is actively transported from the fluid inlet port towards the waste outlet port. For example, the washing fluid may be actively transported from the fluid inlet port towards the waste outlet port by a pump (e.g., peristaltic pump). In some embodiments, the pump is in fluid connection with the fluid inlet port.

The waste outlet port provides an outlet for contaminants, such as cellular debris (e.g., exoskeletal matter, internal organ matter, etc.) bacteria, and the like to be removed from the device to allow for adequate separation of organisms. The waste outlet port may be connected to any suitable container for capturing the waste, which may be discarded as desired.

In some embodiments, the column further comprises a slow flow section proximal to the first end of the column and a rapid flow section proximal to the second end of the column. The rapid flow section has a diameter that is less than the diameter of the slow flow section. The different diameters of the slow flow section and the rapid flow section allow for the flow rate of the washing fluid to be faster in the rapid flow section than the flow rate of the washing fluid in the slow flow section. The flow rate of the washing fluid in the rapid flow section will be faster than the flow rate of the washing fluid in the slow flow section even when the pump (e.g., peristaltic pump) provides a constant flow rate of washing fluid out of the fluid inlet port.

The diameter of the rapid flow section and the slow flow section may be any suitable value, provided that the diameter of the rapid flow section is less than the diameter of the slow flow section. The diameter of each section will depend on the volume of washing fluid to be pumped through the device, the size of helminths and the number of helminths applied to the device, the intended volume of wash solution containing separated helminths to be obtained, the power of the pump, and the like.

Figure 4A:
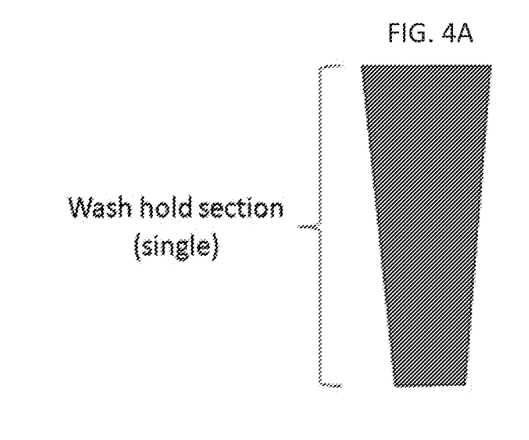
FIG. 4A shows a representative drawing of a single taper wash hold section, in which case HDCs are eluted in a single, Gaussian distribution (FIG. 4B).

In some embodiments, the column further comprises a tapered wash hold section positioned between the slow flow section and the rapid flow section. The tapered wash hold section may comprise a single tapered segment. Alternatively, the tapered wash hold section may comprise two or more tapered segments that taper towards the second end of the column. The tapered wash hold section may be any suitable diameter and number of tapered segments to enable the organisms (e.g., HDCs) to be held in the tapered wash hold section indefinitely until the flow rate out of the fluid inlet port is reduced and the organisms are allowed to elute through the rapid flow section of the column. The variation in diameter and the number of tapered segments of the tapered wash hold section may be selected to allow for organisms (e.g., HDCs) of a wide range of sizes to be held simultaneously in the tapered wash hold section despite substantial variation in the fall speed of the organisms.

In some embodiments, the device further comprises a valve positioned between the fluid inlet port and the second end of the column. The valve may be turned "off" to prevent the flow of washing fluid from the fluid inlet port towards the second end of the column while the column is initially filled with washing fluid. The valve may be turned "on" once the flow of washing fluid from the fluid inlet port towards the second end of the column has been established and the plurality of organisms have been applied to the column to allow for the organisms to pass out of the second end of the column. The valve may comprise any suitable material. For example, the valve may be a polymer valve. Suitable polymer valves include Polytetrafluoroethylene (PTFE), Polyvinylidene Fluoride (PVDF), Polyether Ether Ketone (PEEK), Polypropylene (Polypro), or combinations thereof.

In some embodiments, the device further comprises a removable cap that covers the first end of the column. The cap may comprise any suitable material. The removable cap may be removed from the first end of the column to allow for the composition comprising a plurality of helminths to be applied to the column, and may be subsequently placed back on the column after the composition has been loaded to prevent unwanted contamination from entering the column during use.

In some embodiments, the device further comprises a removable collection vial positioned at the second end of the column. The removable collection vial is used to collect separated organisms (e.g., organisms after they have passed through the column). The removable collection vial may comprise any suitable material that would allow for collection of the organisms without undesired characteristics such as adhesion to the vial, death of the organisms, etc. For example, the removal collection vial may be glass or plastic. The removable collection vial may be coated with an agent to prevent the organisms from sticking to the surface of the vial. In some embodiments, the removable collection vial is sterile. In some embodiments, the removable collection vial is removed from the device and subsequently used for consumption of the contents therein by a subject (e.g., a human).

In some embodiments, the removable collection vial may be hermetically sealed to the column. In such embodiments, the device may further comprise a pressure release valve that would allow for disruption of the hermetic seal and subsequent removal of the collection vial from the device.

In some embodiments, the device further comprises a solid support for holding the column in a vertical position. For example, the device may be attached to a bracket or a stand to hold the column in a vertical (e.g., upright) position.

Other embodiments of the present disclosure include systems for organism separation. The systems for organism separation comprise a plurality of organism separation devices as disclosed herein. The system may comprise any suitable number of organism separation devices (e.g., 2 devices, 3 devices, 4 devices, 5 devices, 6 devices, 7 devices, 8 devices, 9 devices, 10 devices, 20 devices, 30 devices, 40 devices, 50 devices, or more). In some embodiments, the devices are arranged in parallel.

In some embodiments, the system further comprises a pump (e.g., peristaltic pump) in fluid connection with the fluid inlet port for two or more of the devices in the system. The pump actively transports the washing fluid from the fluid inlet ports towards the waste outlet ports of the two or more devices. In some embodiments, the pump is in fluid connection with the fluid inlet port for each device in the system. For example, the system may comprise 10 devices and the pump may be in fluid connection with the fluid inlet port for each device. In other embodiments, the system comprises two or more pumps, such that each pump is in fluid connection with the fluid inlet port for only some of the devices in the system. For example, the system may comprise 10 devices and two pumps, where one pump is in fluid connection with the fluid inlet port for 5 of the devices in the system and the other pump is in fluid connection with the fluid inlet port for the remaining devices in the system. These examples are not in any way to be construed as limiting and are only intended to exemplify representative numbers of devices and pumps that may be present in a system. Any suitable number of devices and any suitable number of pumps may be used in accordance with the systems described herein.

3. Methods for Separating Organisms

Other embodiments of the present disclosure include methods for separating a plurality of organisms. The methods include applying a composition comprising a plurality of organisms to the devices or systems described herein.

The composition may comprise any suitable number of organisms. In some embodiments, composition may comprise 2, 3, 4, 5, 6, 7, 8, 9, 10, about 20, about 30, about 40, about 50, about 60, about 70, about 80, about 90, about 100, about 150, about 200, about 250, about 300, about 350, about 400, about 450, or about 500 organisms. The number of organisms that may be applied to the devices and systems described herein depends on the loading capabilities (e.g. the diameter, the length, or a combination thereof) of the column, as would be appreciated by one of ordinary skill in the art based on the present disclosure. For example, columns of a larger diameter, a longer length, or both may hold more organisms than a column of a thinner diameter or a shorter length without the organisms sticking to the column or to each other.

In some embodiments, the suitable number of organisms applied to the devices and systems may be quantified by the user. In some embodiments, the number of organisms applied to the devices and systems may be automated. For example, various controllers and electronics may be employed to ensure that the number of organisms applied to each machine is suitable without the need for prior or separate quantification (e.g., a human user counting the number of organisms). For example, the composition may be a liquid composition comprising the organisms of interest (e.g., HDCs) and the device may comprise an automated component that applies a pre-determined volume of the liquid composition (e.g., 1 ml, 2 ml, 3 ml, 4 ml, 5 ml, etc.) to the first end of the column. The same volume of liquid may be applied to multiple devices within a system to ensure that the final amount of separated HDCs collected from the second end of the column is comparable across the devices.

In some embodiments, the composition comprises a plurality of helminths. Any suitable helminths may be used in the devices, systems, and methods described herein. Suitable helminths include any desired species of flukes (trematodes), tapeworms (cestodes), or roundworms (nematodes). The selection of the desired species may depend on the intended use of the separated helminths. For example, the selection of the desired helminth may be dependent on the intended disease or condition to be treated with the separated helminths obtained using the devices, systems, and methods described herein.

Exemplary helminths that may be used include, but are not limited to, *Fasciola hepatica, Schistosoma japonicum, Schistosoma mansoni, Clonorchis sinensis, Hymenolepis diminuta, Taenia taeniiformis, Taenia crassiceps, Taenia solium, Echinococcus granulosus, Echinococcus multilocudaris, Acantocheilonema vitae, Brugia malayi, Dirofilaria immitis, Litostomoides sigmoidalis, Onchocerca volvulus, Wuchereria bancrofti, Ancylostoma caninum, Ancylostoma ceylanicum, Heligmosomoides polygyrus, Haemonchus contortus, Necator americanus, Nippostrongylus brasiliensis, Enterobius vermicularis, Syphacia obveolata, Strongyloides stercoralis, Srongyloides venezuelensis, Anisakis simplex, Ascaris lumbricoides, Ascaris suum, Toxocara canis, Trichinella pseudospiralis, Trichinella spiralis, Trichuris muris, Trichuris trichiura,* and *Trichuris suis.* In some embodiments, the helminths are *Hymenolepis diminuta.*

In some embodiments, the composition comprising a plurality of organisms is obtained by a commercial provider of the organisms. In some embodiments, the composition comprising a plurality of organisms is obtained by extracting the organisms from an intermediate host. Suitable methods for obtaining a composition comprising a plurality of organisms are described in Smyth et al., *J Clin Med.* 2017; 6(10): 98, the entire contents of which are incorporated herein by reference. For example, a composition containing a plurality of helminths may be obtained by extracting the helminths from an insect, such as a grain beetle, that has been previously infected with the helminth eggs. The helminths may be extracted from the insect at the egg stage, the larval stage, or the adult stage and subsequently applied to the devices or systems described herein to obtain separated helminths. In some embodiments, the helminths are extracted from the intermediate host at the larval stage and the larvae are added to the devices and systems described herein. For example, for separation of HDCs, *Hymenolepis diminuta* larvae (e.g., cysticercoids) may be applied to the devices and columns described herein.

In some embodiments, the method includes applying the composition to the first end of the washing device while the washing fluid is actively transported from the fluid inlet port towards the waste outlet port at a first flow rate. For example, the method may include starting (e.g., turning "on") the pump to initiate the movement of washing fluid from the fluid inlet port towards the waste outlet port at a first flow rate, and subsequently applying the composition comprising a plurality of organisms to the first end of the washing device. Applying the composition to the first end of the washing device after movement of the washing fluid from the fluid outlet port towards the waste outlet port has been established helps to avoid undesired sticking of the organisms to a surface of the device.

In some embodiments, the method may include turning a valve positioned in between the fluid outlet port and the second end of the column "off" to prevent the flow of washing fluid from the fluid inlet port towards the second end of the column while the column is initially filled with washing fluid. The valve may be turned "on" once the flow of washing fluid from the fluid inlet port towards the second end of the column has been established and the plurality of organisms have been applied to the column. Turning the valve "on" would thus allow for the organisms to flow out of the second end of the column, such as out of the second end of the column and into a removable collection device, with minimal risk of sticking to the column itself or to the valve.

In some embodiments, the method may include reducing the flow rate from the fluid inlet port to a second flow rate. The flow rate may be reduced to a second flow rate at any suitable time. For example, the flow rate may be reduced to a second flow rate after a suitable number of organisms have been collected in the tapered wash hold section of the column. In some embodiments, reducing the flow rate to the second flow rate allows for the collected organisms to pass through the remainder of the column (e.g., pass through the rapid flow section) and out of the second end of the column. For example, reducing the flow rate to the second flow rate allows for the organisms collected in the wash hold section to pass through the rapid hold section and out of the second end of the column into a suitable collection vial.

In some embodiments, the method may comprise visually inspecting the column to determine whether a suitable number of organisms have collected in the tapered wash hold section of the column, and subsequently reducing the flow rate to a second flow rate to allow for elution of the organisms. In some embodiments, the method may comprise reducing the flow rate to a second flow rate after a predetermined amount of time from adding the composition comprising a plurality of organisms to the first end of the device.

The first flow rate and the second flow rate may be any suitable rate to allow for separation of organisms with minimal damage to the organisms themselves. For example, the first flow rate may be 4.5 ml/minute and the second flow rate may be any suitable value lower than 4.5 ml/minute. In some embodiments, the first flow rate is 4.5 ml/minute, and the second flow rate is 2.0 ml/minute. As described above, the difference in diameter between the various sections of the column allow for differential flow speeds between the slow flow section, the wash hold section, and the rapid flow section. For example, the pump may be set to provide a first flow rate of 4.5 ml/minute, which may cause a first flow speed in the slow flow section of 0.04 cm/s-0.2 cm/s. The pump may be reduced to a second flow rate of 2.0 ml/minute, which allows for a flow speed in the rapid flow section of <0.04 cm/s.

The methods described herein allow for collection of a plurality or microorganisms that have been separated from at least one other contaminant in the composition containing the plurality or organisms. For example, the organisms collected from the second end of the column may be separated from components including cellular debris (e.g., exoskeletal matter, internal organ matter, etc.), bacteria, and the like, that were present in the initial composition added to the column. For example, the method may allow for collecting a plurality of separated helminths that are substantially free of bacteria. Accordingly, the methods described herein may allow for production of solutions containing a plurality of helminths in a suitable liquid (e.g., the washing buffer) that are suitable for subsequent consumption by a subject.

The devices and systems described herein may be capable of generating helminthic cysts at a suitable rate for clinical therapeutic dosing (>1000 HDCs/day) with a bacterial load of ≤10 CFU/ml to far exceed the FDA guidelines that require ≤100 CFU/ml.

4. Examples

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties. The present disclosure has multiple aspects, illustrated by the following non-limiting examples.

Figure 1:
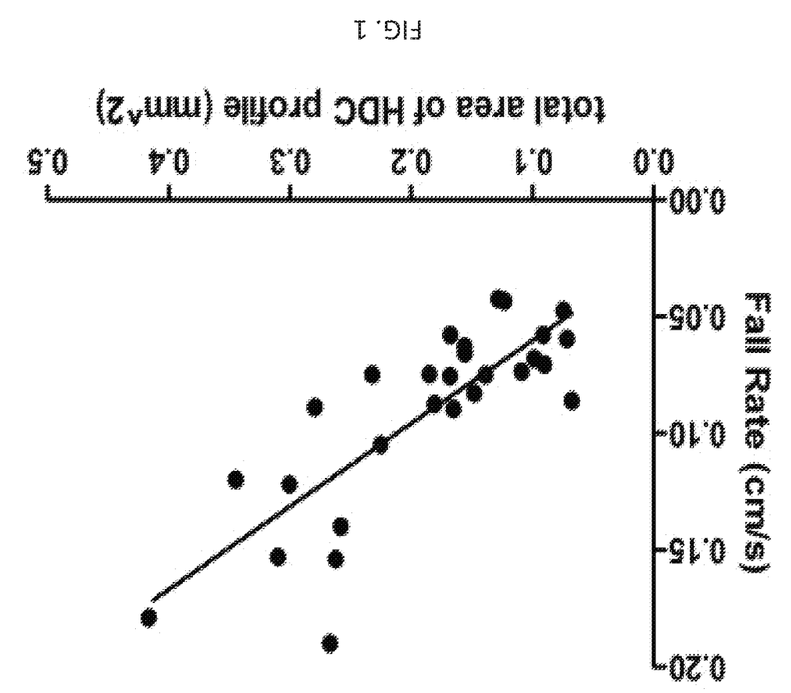
FIG. 1 is a graph showing the fall speed through aqueous solution as a function of HDC size in accordance with one embodiment of the present disclosure. HDC size (as measured by the total area of the HDC in profile) varies over more than a 5-fold range, and is strongly correlated ($r^2=0.65$, $p<0.0001$) with the fall rate, which ranges from 0.04 to 0.19 cm/s.

The fall speed rate of HDCs through an aqueous solution as a function of HDC size was measured. It was found that HDC size (as measured by the total area of the HDC in profile) varies over more than a 5-fold range, and is strongly correlated ($r^2=0.65$, $p<0.0001$) with the fall rate which ranges from 0.04 to 0.19 cm/s. Based on these results, a variable width column where the speed of flow through the column at a constant flow rate is adjusted by varying the diameter in the column was developed.

One embodiment of the organism separation device described herein is shown in FIG. 2. As shown, the organism separation device (100) comprises a cylindrical column (110) having a first end (120) for receiving a plurality of organisms, a second end (130) distal to the first end, a fluid inlet port (140) proximal to the second end of the column for receiving washing fluid, and a waste outlet port (150) proximal to the first end of the column.

Another embodiment of the organism separation device is shown in FIG. 3. In some embodiments, the organism separation device (100) further comprises a slow flow section (210) proximal to the first end of the column, a rapid flow section (230) proximal to the second end of the column and having a diameter that is less than the slow flow section; and a tapered wash hold section (220) positioned between the slow flow section and the rapid flow section. The washing column is designed to hold HDCs in the wash hold section (flow speed constant but ranging from 0.04 cm/s-0.2 cm/s in that section) while on wash phase, but allows HDCs to elute through the rapid flow section (flow speed<0.04 cm/s in that section) during the elution phase. Blue color indicates liquid levels. (HDCs remain in liquid throughout the process.)

The organisms (e.g., HDCs) may be eluted into a removable collection vial. The vial may be hermetically sealed to the column. A pressure release valve may be provided on the removable collection vial for efficient removal from the device. In addition, accessories such as holding clamps and a peristaltic pump to move the liquid up the column may be used.

Figure 4B:
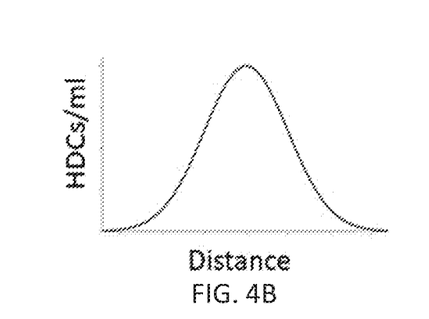
FIG. 4C shows a representative drawing of a wash hold section with multiple tapered segments separated by un-tapered segments (showing three tapered segments as an example). This design allows for separation of different "grades" of HDCs based on their fall speed in solution, which is a function of helminth size (FIG. 4D).
Figure 4C:
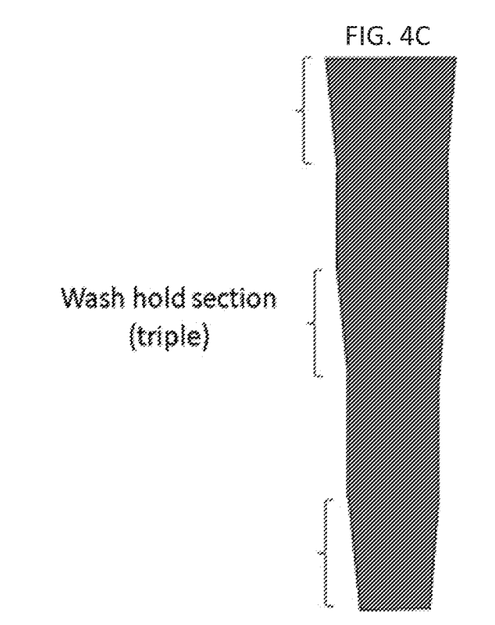
Figure 4D:
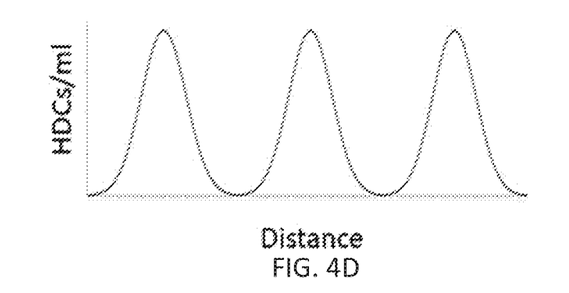

Other embodiments of the organism separation device is shown in FIG. 4A-D. FIG. 4A shows a representative drawing of a single taper wash hold section, in which case HDCs are eluted in a single, Gaussian distribution (FIG. 4B). FIG. 4C shows a representative drawing of a wash hold section with multiple tapered segments separated by un-tapered segments (showing three tapered segments as an example). This design allows for separation of different "grades" of HDCs based on their fall speed in solution, which is a function of helminth size (FIG. 4D).

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

What is claimed is:

1. A method of separating microorganisms, the method comprising:
   a) applying a composition comprising a plurality of microorganisms and one or more contaminants to a device comprising:
      a column having a first end for receiving the composition and a second end distal to the first end,
      a fluid inlet port proximal to the second end of the column for receiving washing fluid, and a waste outlet port proximal to the first end of the column;

b) applying a washing fluid to the device via the fluid inlet port; and c) actively transporting the washing fluid and contaminants contained therein to the waste outlet port using a pump as the plurality of microorganisms passes from the first end to the second end of the column counter to the flow of the washing fluid, thereby separating the plurality of microorganisms from contaminants in the composition.

2. The method of claim 1, wherein the first end comprises a first opening for receiving the composition and wherein the second end comprises a second opening for collecting the plurality of organisms, wherein the first opening has a diameter greater than the second opening.

3. The method of claim 1, wherein the column comprises:
a slow flow section proximal to the first end of the column, wherein the slow flow section is defined by a first diameter,
a rapid flow section proximal to the second end of the column, wherein the rapid flow section is defined by a second diameter that is less than the first diameter; and
a tapered wash hold section positioned between the slow flow section and the rapid flow section.

4. The method of claim 3, wherein the tapered wash hold section comprises a single tapered segment.

5. The method of claim 3, wherein the tapered wash hold section comprises two or more tapered segments that taper towards the second end of the column.

6. The method of claim 1, wherein the device further comprises a valve positioned between the fluid inlet port and the second end.

7. The method of claim 1, wherein the device further comprises a removable cap that covers the first end.

8. The method of claim 1, wherein the device further comprises a pump in fluid connection with the fluid inlet port for actively transporting the washing fluid from the fluid inlet port towards the waste outlet port.

9. The method of claim 1, wherein the device further comprises a removable collection vial positioned at the second end of the column.

10. The method claim 1, wherein the device further comprises a solid support for holding the column in a vertical position.

11. The method of claim 1, wherein the organism separation device is comprised in a system including a plurality of organism separation devices, each device comprising components a), b), and c) as described in claim 1.

12. The method of claim 11, wherein the devices in the system are arranged in parallel.

13. The method of claim 11, wherein the system further comprises a pump in fluid connection with the fluid inlet port for two or more of the devices in the system, wherein the pump actively transports the washing fluid from the fluid inlet ports to the waste outlet ports of the two or more devices.

14. The method of claim 1, comprising:
a) applying the composition to the first end of the column while the washing fluid is actively transported from the fluid inlet port to the waste outlet port at a first flow rate;
b) reducing the flow rate from the fluid inlet port to a second flow rate; and
c) collecting the plurality of organisms from the second end of the column;
wherein the plurality of organisms have been separated from at least one other component in the washing fluid.

15. The method of claim 14, wherein the washing fluid comprises at least 0.5% protein (w/w).

16. The method of claim 14, wherein the plurality of organisms are helminths.

17. The method of claim 16, wherein the helminths are *Hymenolepis diminuta* cysticercoids (HDCs).

18. The method of claim 16, wherein the plurality of helminths collected from the second end of the column are substantially free of bacteria.

19. A composition comprising separated helminths obtained by the method of claim 14.

* * * * *